(12) United States Patent
Kim et al.

(10) Patent No.: US 11,623,910 B1
(45) Date of Patent: Apr. 11, 2023

(54) **COMPOUND ISOLATED FROM *TORILIDIS FRUCTUS*, AND ANTICANCER PHARMACEUTICAL COMPOSITION CONTAINING SAME AS ACTIVE INGREDIENT**

(71) Applicants: PHARMA-GENE CO., LTD., Daejeon (KR); J-MEDIZIN CO., LTD, Daejeon (KR)

(72) Inventors: Young-Min Kim, Daejeon (KR); Hae-Kyung Suh, Daejeon (KR)

(73) Assignees: PHARMA-GENE CO., LTD., Daejeon (KR); J-MEDIZIN CO., LTD, Daejeon (KR)

(*) Notice: Subject to any disclaimer, the term of this patent is extended or adjusted under 35 U.S.C. 154(b) by 0 days.

(21) Appl. No.: 17/799,291

(22) PCT Filed: Feb. 15, 2021

(86) PCT No.: PCT/KR2021/001878
§ 371 (c)(1),
(2) Date: Aug. 12, 2022

(87) PCT Pub. No.: WO2021/162505
PCT Pub. Date: Aug. 19, 2021

(30) Foreign Application Priority Data

Feb. 13, 2020 (KR) .................. 10-2020-0017808

(51) Int. Cl.
*C07C 69/28* (2006.01)
*A23L 33/105* (2016.01)
*A61P 35/00* (2006.01)

(52) U.S. Cl.
CPC .......... *C07C 69/28* (2013.01); *A23L 33/105* (2016.08); *A61P 35/00* (2018.01); *A23V 2002/00* (2013.01)

(58) Field of Classification Search
None
See application file for complete search history.

(56) References Cited

FOREIGN PATENT DOCUMENTS

| KR | 10-0159642 B1 | 12/1998 |
| KR | 10-1484709 B1 | 1/2015 |
| KR | 10-1485318 B1 | 1/2015 |
| WO | 2008-144942 A1 | 12/2008 |

OTHER PUBLICATIONS

Cheng et al., Chinese Journal of Organic Chemistry (2018), 38, pp. 1829-1832.*
International Search Report for PCT/KR2021/001878 dated May 20, 2021 from Korean Intellectual Property Office.
Dong Chun Kim et al., "Guaiane Sesquiterpenoids Isolated from the Fruits of Torilis japonica and Their Cytotoxic Activity", Helvetica Chimica Acta, vol. 93, Issue4, Apr. 2010, pp. 692-697.
Masao Nakazaki et al., "The Structure of Torilin", Tetrahedron, vol. 7, No. 37, 1966, pp. 4499-4504.
Hye Won Park et al., "Guaiane sesquiterpenoids from Torilis japonica and their cytotoxic effects on human cancer cell ines", Archives of Pharmacal Research, vol. 29, No. 2, 2006, pp. 131-134.
Xin Li et al., "Virtual Screening Based on Ensemble Docking Targeting Wild-Type p53 for Anticancer Drug Discovery", Chemistry & Biodivesity, vol. 16, Issue7, May 28, 2019, e1900170, pp. 1-9.
In-Kyoung Lee et al., "New Guaiane Sesquiterpenes from the Fruits of Torilis japonica", Chemical and Pharmaceutical Bulletin, vol. 56, Issue 10, 2008, pp. 1483-1485.

* cited by examiner

*Primary Examiner* — Brian J Davis
(74) *Attorney, Agent, or Firm* — Revolution IP, PLLC (57) ABSTRACT

The present invention relates to a compound isolated from Torilidis Fructus, and an anticancer pharmaceutical composition containing same as an active ingredient, wherein the compound of the present invention has effects of reducing the viability of various types of cancer cells, having no effect on the cell viability of normal cells and reducing the tumor size and weight of lung cancer and colorectal cancer when used in an animal model. Therefore, the compound according to the present invention can be usefully used in anticancer drugs or health functional food industries.

7 Claims, 10 Drawing Sheets

COMPOUND ISOLATED FROM *TORILIDIS FRUCTUS*, AND ANTICANCER PHARMACEUTICAL COMPOSITION CONTAINING SAME AS ACTIVE INGREDIENT

DESCRIPTION

Technical Field

The present invention relates to a compound isolated from Torilidis Fructus and an anticancer pharmaceutical composition containing same as an active ingredient.

Background Art

Despite decades of efforts, cancer still ranks first or second among the causes of death among modern people due to disease. Such cancers are developed by genetic mutations caused by carcinogens or viruses in normal cells. The development and treatment of anticancer drugs have been developed to target genes or proteins that are not expressed in normal cells but are specifically expressed only in cancer cells. Anticancer drugs are the most common and effective treatment methods for cancer treatment, either alone or in combination with other therapies such as radiotherapy. Treatment of cancer with these anticancer agents is due to their ability to kill cancer cells, and it kills not only cancer cells but also normal cells, which frequently causes side effects such as hair loss, loss of appetite, nausea, vomiting, dyspnea, stomatitis, and neutropenic fever. Depending on the patient's general health, such side effects may make cancer treatment impossible, or at least cause extreme displeasure and discomfort to the patient, and seriously impair the cancer patient's quality of life.

On the other hand, Torilidis Fructus is the fruit of *Torilis japonica* (Houtt.) DC., which is a biennial plant in the Umbelliferae family, and is known for its spicy, bitter and warm nature and non-poisonous. It is also called 'Bamdorat' in Korean. It grows mainly in ditches or wetlands, and it is said that the name Torilidis Fructus was given to snakes hiding in the grass of the Torilidis Fructus and eating the seeds. It is 30 to 70 cm high and has hairs all over it. The leaves are pinnately compound leaves, 5 to 10 cm long, with a sharp tip, and the tip of the petiole wraps around the main stem. The fruit is 4 to 6 mm long, looks like rice seed, and has dense thorn hairs on the outside.

In oriental medicine, a herbal medicine made from its dried fruits is called Torilidis Fructus(or sasangja), and its pharmacological effects include antiparasitic action and sex hormone-like action. It is used as an anti-inflammatory agent or an ointment to relieve itching because it is effective in the treatment of leukorrhea in women, etc., and is effective in skin pruritus by inhibiting the activity of influenza virus and Trichomonas bacteria. In addition, the Torilidis Fructus is also used for skin eczema and allergic dermatitis because it has a therapeutic effect on skin diseases. It is reported that the main component of the Torilidis Fructus contains sesquiterpene compounds such as torilin and torilolone.

On the other hand, Korean Patent No. 0159642 discloses a composition for enhancing anticancer drug activity containing torilin, Korean Patent No. 1484709 discloses a composition for immune enhancement and treatment or prevention of cancer containing *Cnidium monnieri* extract as an active ingredient, and Korea Patent No. 1485318 discloses a food composition and pharmaceutical composition for preventing or improving cancer containing Torilidis Fructus extract as an active ingredient. However, there is no disclosure of the compound isolated from Torilidis Fructus of the present invention and an anticancer pharmaceutical composition comprising the same as an active ingredient.

DISCLOSURE

Technical Problem

The present invention has been derived from the above needs, and the present invention provides a compound isolated from Torilidis Fructus and an anticancer pharmaceutical composition comprising the same as an active ingredient. The present invention was completed by confirming that the compound of the present invention has the effect of reducing the viability of various types of cancer cells without affecting the cell viability of normal cells, and reducing the tumor size and weight of lung cancer and colorectal cancer when used in an animal model.

Technical Solution

In order to achieve the above objects, the present invention provides a compound of Formula 1 or a pharmaceutically acceptable salt thereof.

Further, the present invention provides an anticancer pharmaceutical composition comprising a torilin derivative compound of Formula 1 or Formula 2, or a pharmaceutically acceptable salt thereof, as an active ingredient.

Further, the present invention provides an anticancer health functional food composition comprising the torilin derivative compound of Formula 1 or Formula 2, or a food acceptable salt thereof, as an active ingredient.

Advantageous Effects

The present invention relates to a compound isolated from Torilidis Fructus and an anticancer pharmaceutical composition containing same as an active ingredient, and the compound of the present invention has the effect of reducing the viability of various types of cancer cells without affecting the cell viability of normal cells, and reducing the tumor size and weight of lung cancer and colorectal cancer when used in an animal model.

BEST MODE

The present invention relates to a compound represented by Formula 1 or a pharmaceutically acceptable salt thereof.

[Formula 1]

Further, the present invention relates to an anticancer pharmaceutical composition comprising the torilin derivative compound represented by Formula 1 or Formula 2, or a pharmaceutically acceptable salt thereof, as an active ingredient.

[Formula 1]

[26]
[27]

[Formula 2]

[28]

The torilin derivative compounds of the above Formula 1 and Formula 2 are preferably isolated from Torilidis Fructus, but are not limited thereto, and may be isolated from natural products other than Torilidis Fructus, or synthesized by organic synthesis.

The anticancer is to any one cancer selected from lung cancer, gastric cancer, liver cancer, breast cancer, colorectal cancer and pancreatic cancer, but limited thereto.

The pharmaceutical composition of the present invention may be in various oral or parenteral formulations. When formulating the composition, it may be prepared by using carriers, excipients or diluents commonly used, but not limited thereto.

Solid formulations for oral administration include tablets, pills, powders, granules, capsules, etc., and such solid preparations are prepared by mixing one or more compounds with at least one excipient, for example, starch, calcium carbonate, sucrose or lactose, gelatin, etc. Further, in addition to simple excipients, lubricants such as magnesium stearate and talc are also used. Liquid formulations for oral administration include suspensions, oral liquids, emulsions, or syrups. In addition to commonly used simple diluents such as water and liquid paraffin, various excipients such as wetting agents, sweeteners, fragrances or preservatives may be included.

Formulations for parenteral administration include sterile aqueous solutions, non-aqueous solvents, suspension agents, emulsions, lyophilized formulations or suppositories. The non-aqueous solvents and the suspension agents may include propylene glycol, polyethylene glycol, vegetable oils such as olive oil, and injectable esters such as ethyl oleate. As the base of the suppository, witepsol, macrogol, tween 61, cacao butter, laurin fat, glycerol, gelatin and the like may be used.

The pharmaceutical composition of the present invention can be administered orally or parenterally, and when administered parenterally, it is preferable to select an external skin application, or intraperitoneal, rectal, intravenous, intramuscular, subcutaneous, intrauterine epidural or intracerebrovascular injection method, but limited thereto.

The pharmaceutical composition of the present invention is administered in a pharmaceutically effective amount. In the present invention, the pharmaceutically effective amount means an amount sufficient to treat a disease with a reasonable benefit/risk ratio applicable to medical treatment, and the effective dose level can be determined according to factors including patient's disease type, severity, drug activity, drug sensitivity, administration time, administration route and excretion rate, duration of treatment, concurrent drugs, and other factors well known in the medical field. The composition of the present invention may be administered as an individual therapeutic agent or in combination with other therapeutic agents, may be administered sequentially or simultaneously with conventional therapeutic agents, and may be administered single or multiple doses. In consideration of all of the above factors, it is important to administer an amount that can obtain the maximum effect with a minimum amount without side effects, which can be easily determined by those skilled in the art.

The dosage of the composition of the present invention may be administered in various ranges depending on the patient's weight, age, sex, health status and diet, administration time, administration method, excretion rate, and severity of disease. However, since it may increase or decrease depending on administration route, severity of obesity, sex, weight, age, etc., the dosage is not intended to limit the scope of the present invention in any way.

Further, the present invention relates to an anticancer health functional food composition comprising the torilin derivative compound represented by Formula 1 or Formula 2, or a food acceptable salt thereof, as an active ingredient.

The health functional food composition of the present invention can be added to food as it is or used with other food or food ingredients, and can be used appropriately in a conventional manner. The mixing amount of the active ingredient may be appropriately determined depending on the purpose of its use(for prevention or improvement). In general, the amount of the compound contained in the health functional food may be added in an amount of 0.1 to 90 parts by weight based on the total weight of the health functional food. However, in the case of long-term ingestion for health and hygiene purposes or for health control, the amount may be less than or equal to the above range, and an amount greater than or equal to the above range may also be used.

When the health functional food composition of the present invention is used as a beverage, there is no particular limitation on other ingredients other than containing the compound as an active ingredient, and it may contain various flavoring agents or natural carbohydrates as additional ingredients like conventional beverages. Examples of the natural carbohydrate include monosaccharides, for example, glucose, fructose and the like; disaccharides, for example, maltose, sucrose and the like; and polysaccharides, for example, conventional sugars such as dextrin, cyclodextrin and the like, and sugar alcohols such as xylitol, sorbitol, erythritol and the like. As flavoring agents other than those described above, natural flavoring agents (taumatine, stevia extract (eg, rebaudioside A, glycyrrhizin, etc.)) and synthetic flavoring agents (saccharin, aspartame, etc.) can be used advantageously.

In addition to the active ingredient, the health functional food composition of the present invention may further comprises at least one selected from nutrients, vitamins, electrolytes, flavoring agents, colorants, enhancers, pectic acid and a salt thereof, alginic acid and a salt thereof, organic acids, protective colloidal thickening agents, pH adjusting agents, stabilizers, preservatives, glycerin, alcohols, and carbonating agents used in carbonated beverages. In addition, the health functional food composition of the present invention may contain the pulp for the production of natural fruit juice and vegetable beverage. The pulp may be used independently or in combination. Although the ratio of the various additives is not critical, it is generally selected in the range of 0.1 to 20 parts by weight per 100 parts by weight of the compound of the present invention.

Hereinafter, the present invention will be described in more detail through examples. It will be apparent to those skilled in the art that these examples are only for illustrating the present invention in more detail and the scope of the present invention is not limited to these examples.

EXAMPLE 1. ISOLATION AND PURIFICATION OF SINGLE SUBSTANCE FROM TORILIDIS FRUCTUS

After fractionation using an organic solvent was carried out from the Torilidis Fructus extract to isolate and purify a single substance from the n-hexane fraction, the structure of the isolated single substance (compound) was confirmed by mass spectrometry and NMR analysis.

The n-hexane fraction was subjected to silica gel flash column chromatography, silica gel open column chromatography, Sephadex LH-20 column chromatography, reverse phase (ODS) MPLC (medium pressure liquid chromatography), and HPLC to purely isolate and purify a compound (Tr-9).

Figure 1:
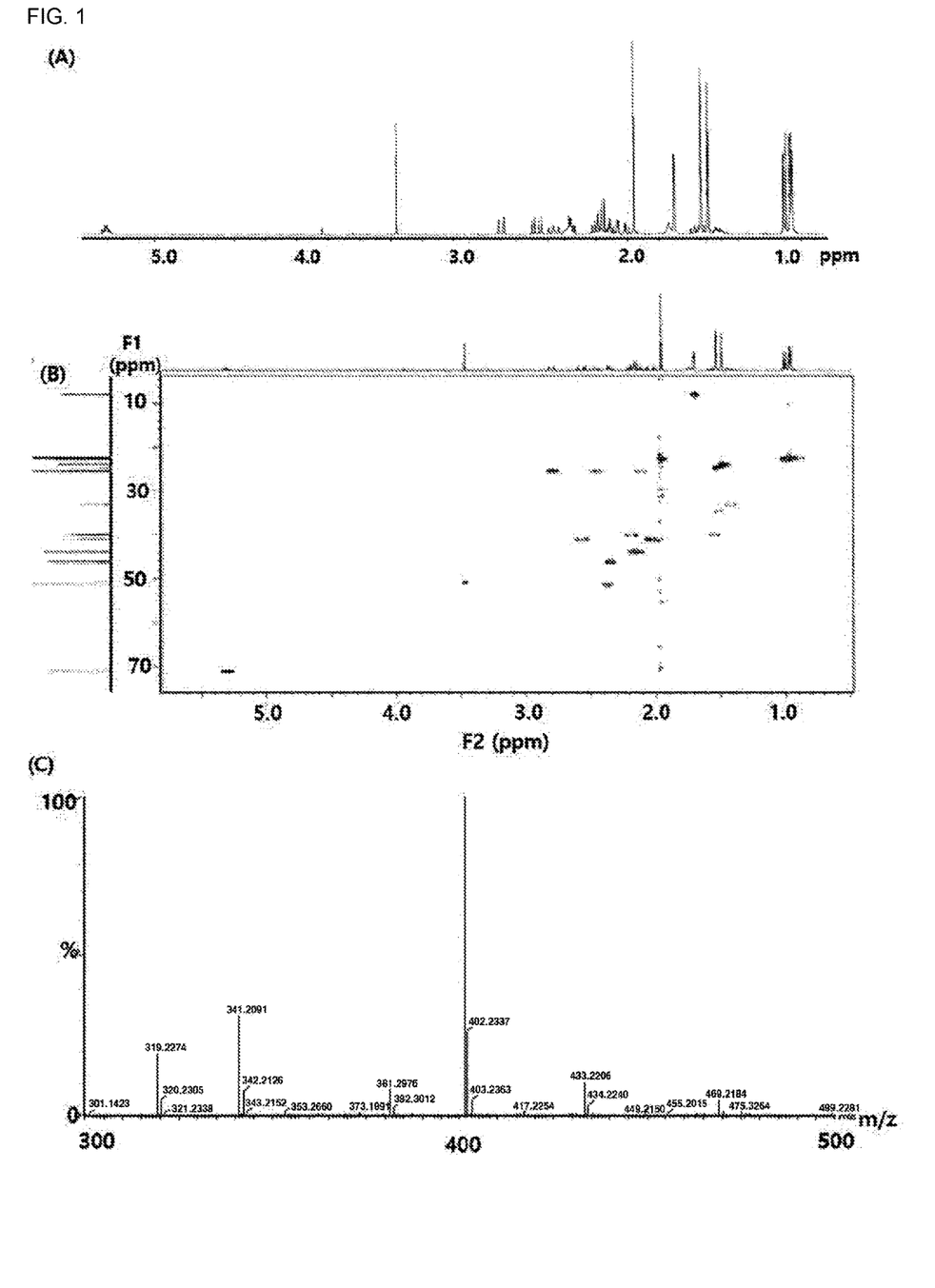
FIG. 1 shows 1H-NMR(A), HMQC(B) and mass spectrum(C) of the Tr-9 compound.
Figure 2:
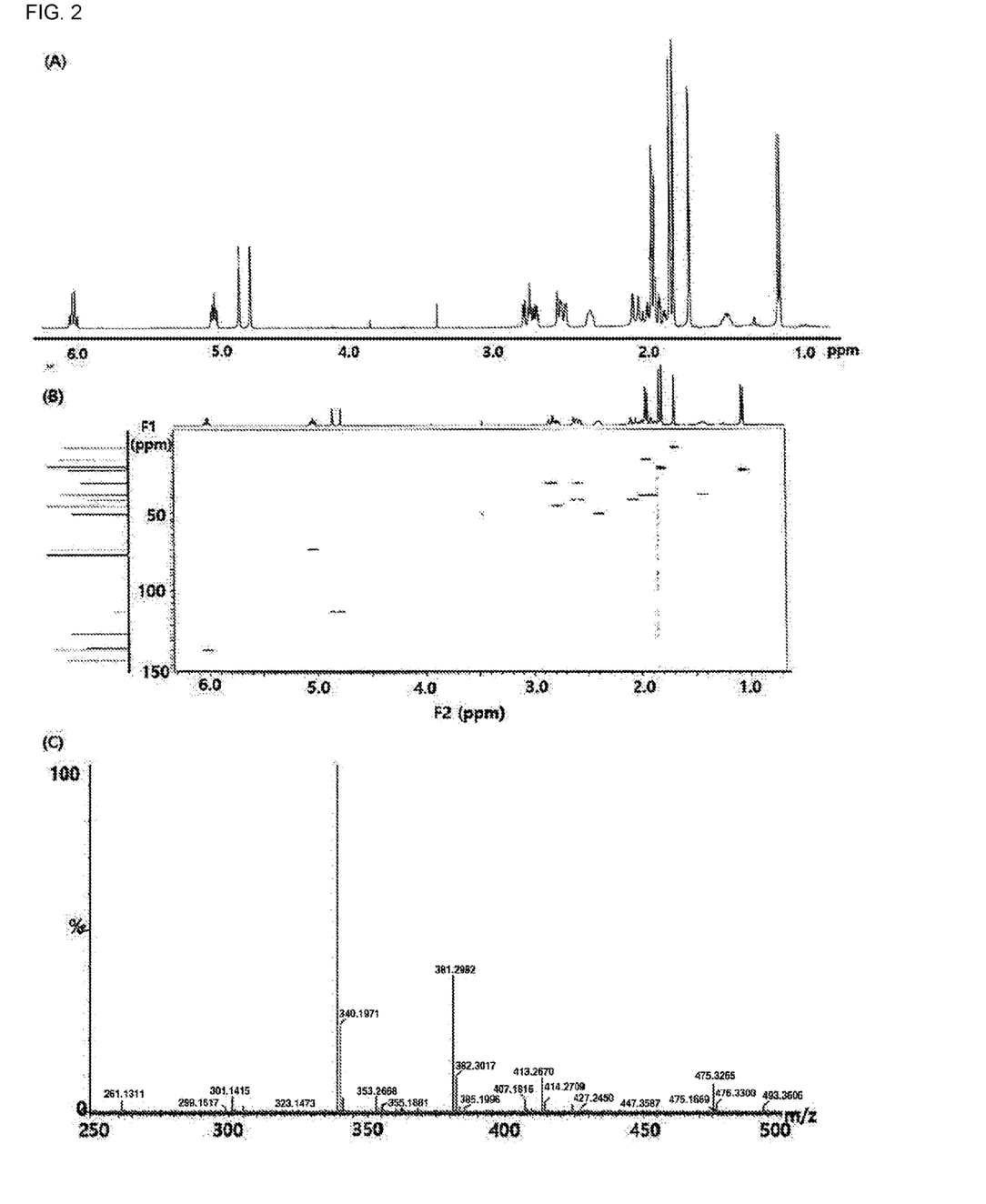
FIG. 2 shows 1H-NMR(A), HMQC(B) and mass spectrum(C) of the Tr-10 compound.
Figure 3:
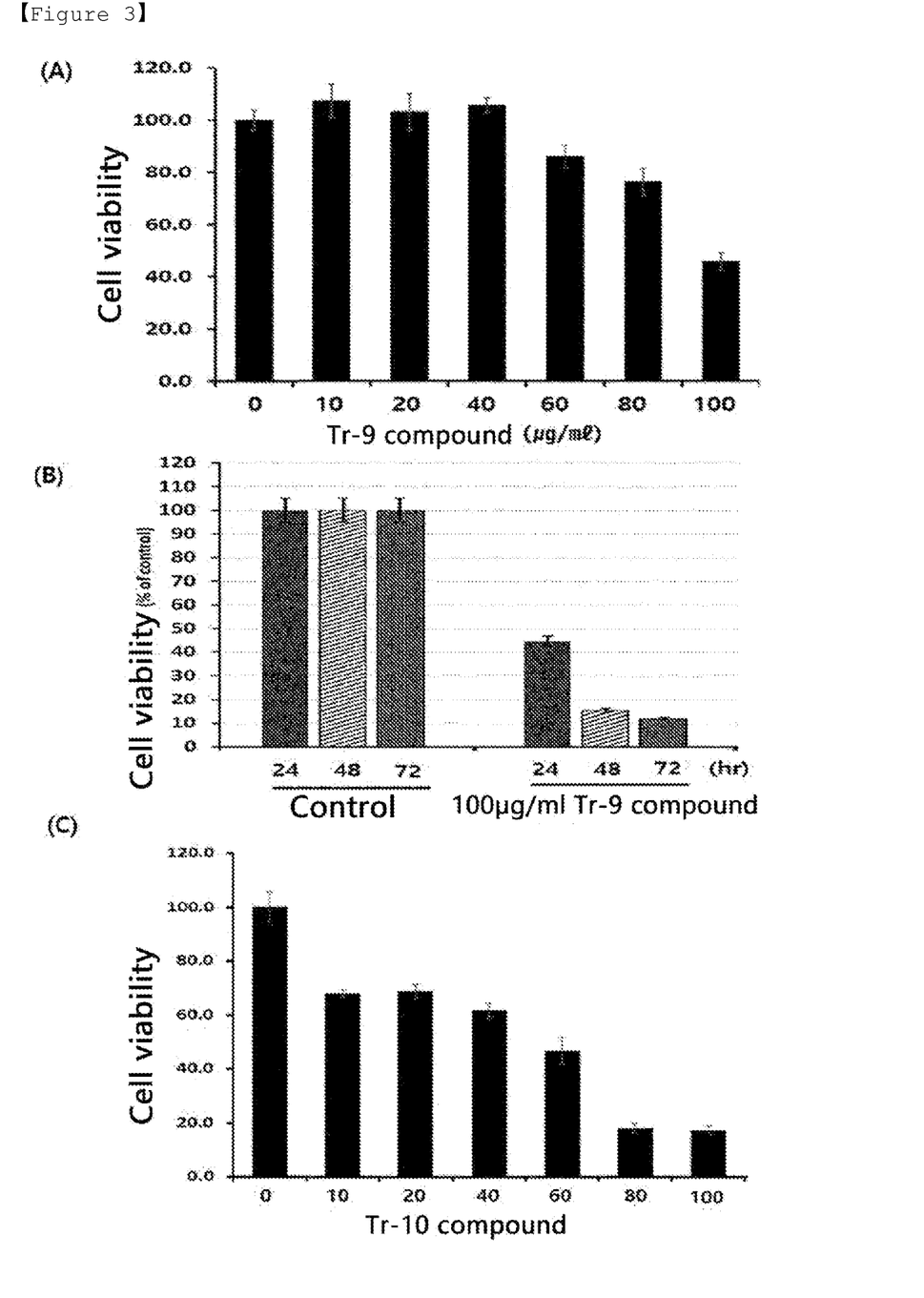
FIG. 3 shows cell viability of the lung cancer cell line (A549) according to the treatment by concentration of the Tr-9 compound(A) and the Tr-10 compound(C) and the treatment by time the Tr-9 compound(B).
Figure 4:
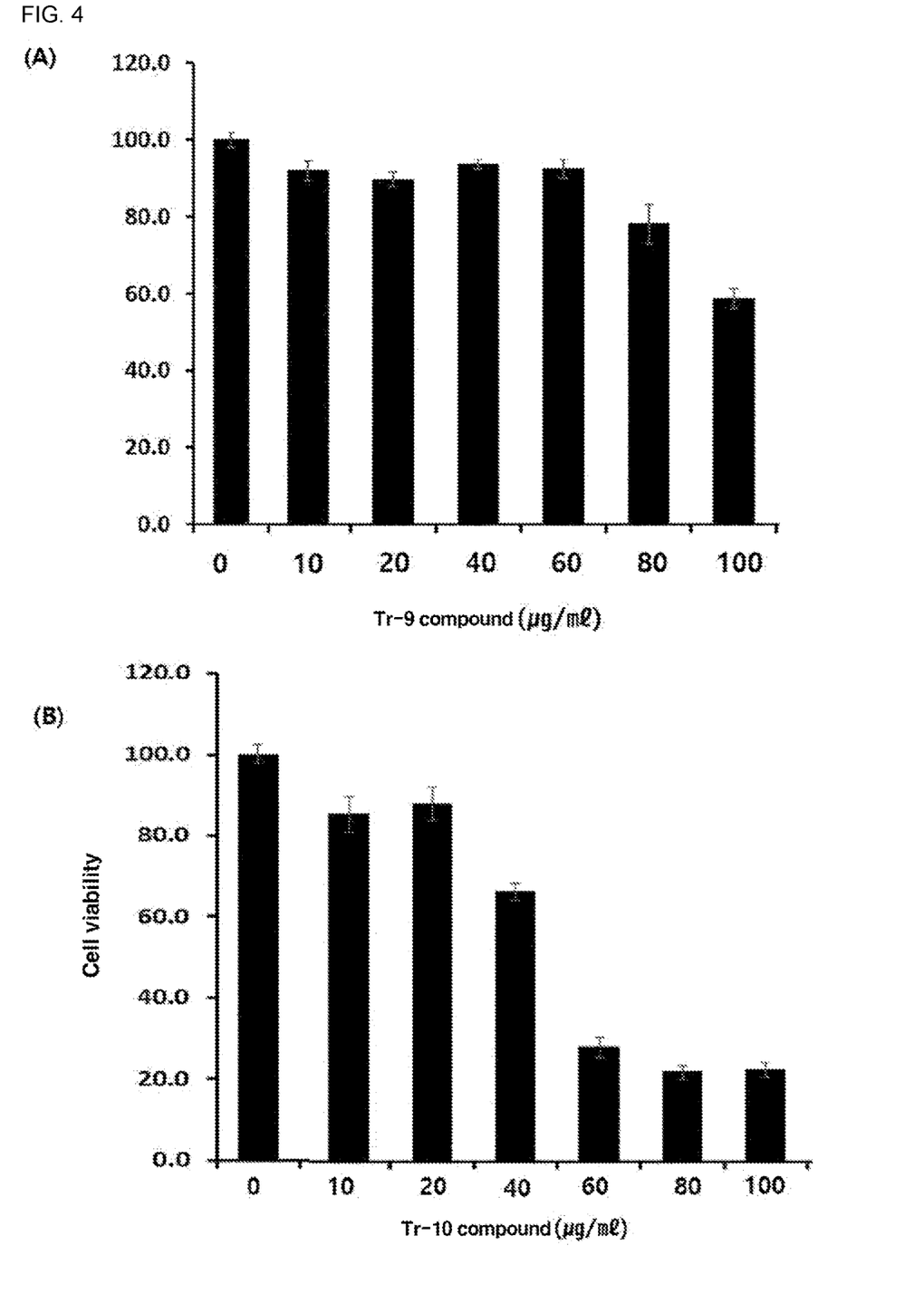
FIG. 4 shows cell viability of the gastric cancer cell line (AGS) according to the treatment by concentration of the Tr-9 compound(A) and the Tr-10 compound(B).
Figure 5:
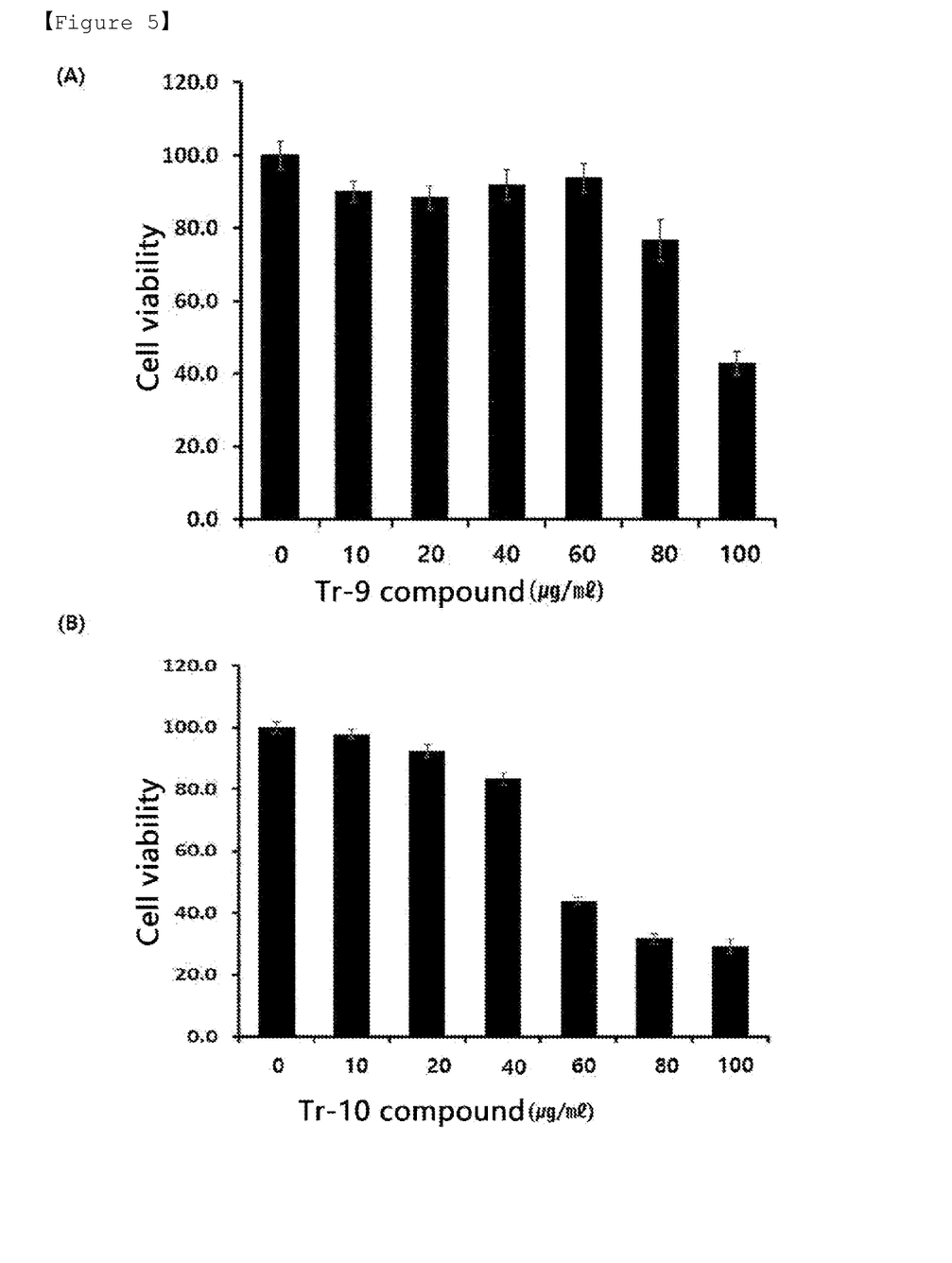
FIG. 5 shows cell viability of the breast cancer cell line (MDA-MB-231) according to the treatment by concentration of the Tr-9 compound(A) and the Tr-10 compound(B).
Figure 6:
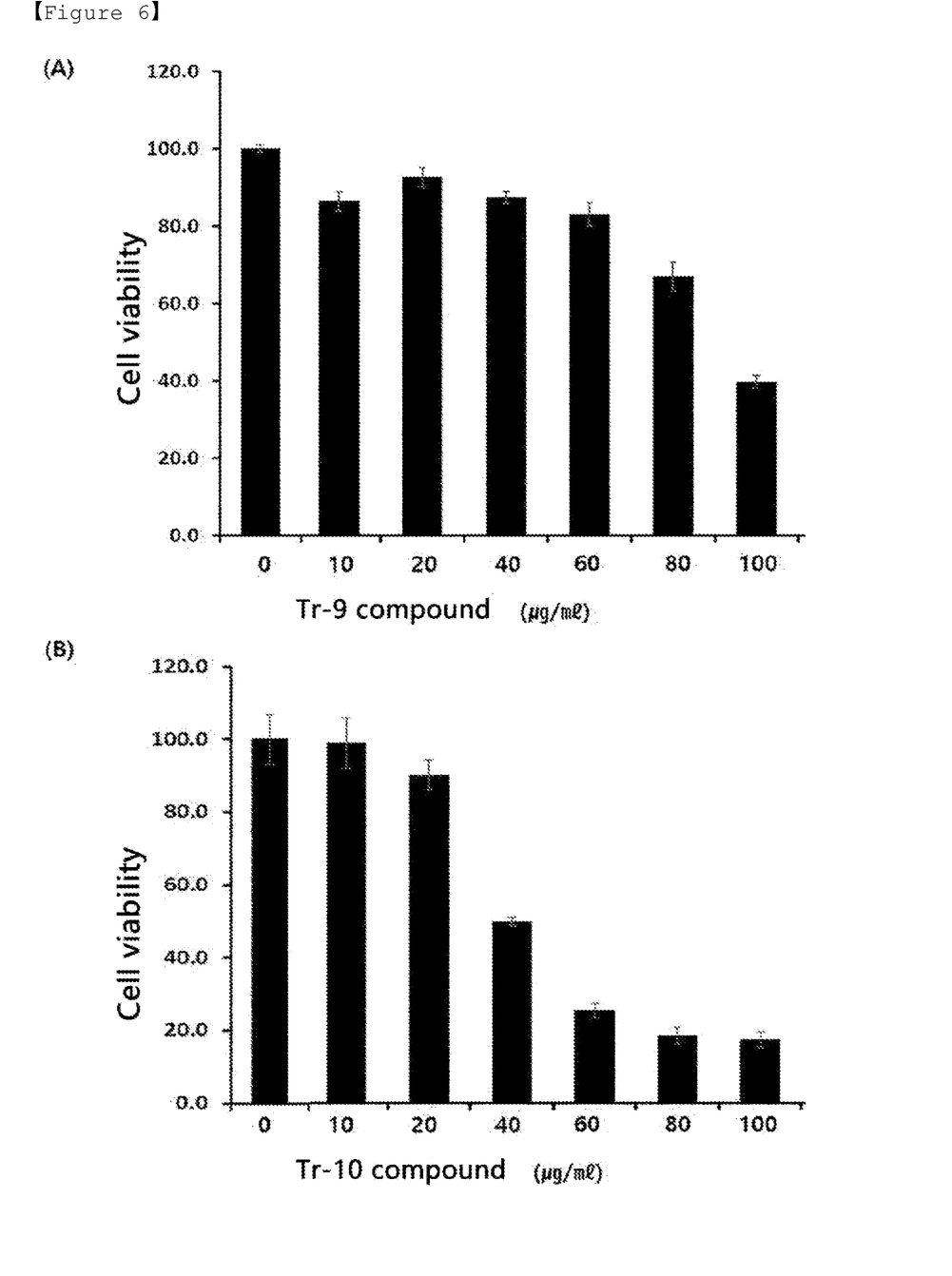
FIG. 6 shows cell viability of the liver cancer cell line (Hep3B) according to the treatment by concentration of the Tr-9 compound(A) and the Tr-10 compound(B).
Figure 7:
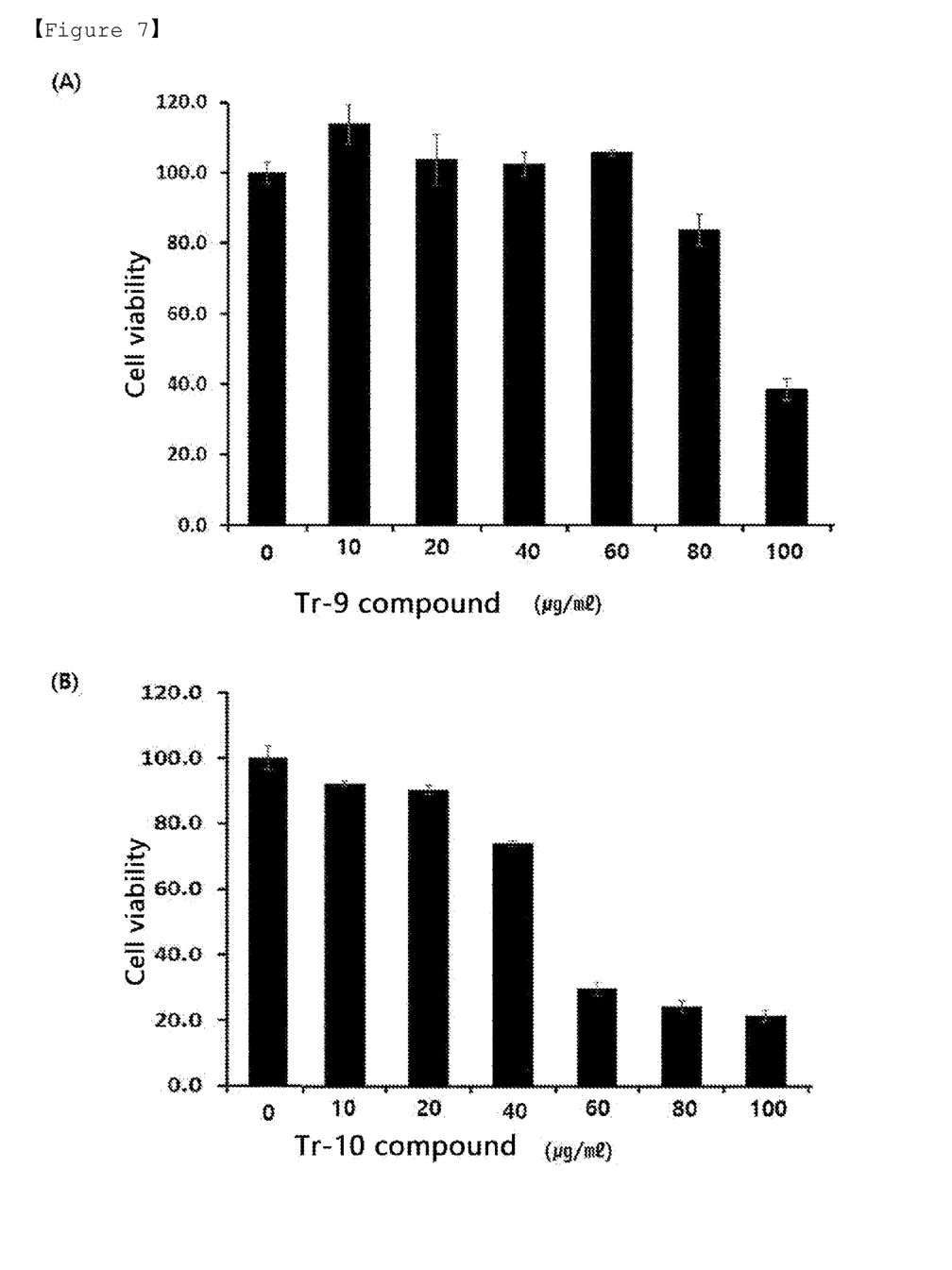
FIG. 7 shows cell viability of the colorectal cancer cell line (HCT116) according to the treatment by concentration of the Tr-9 compound(A) and the Tr-10 compound(B).
Figure 8:
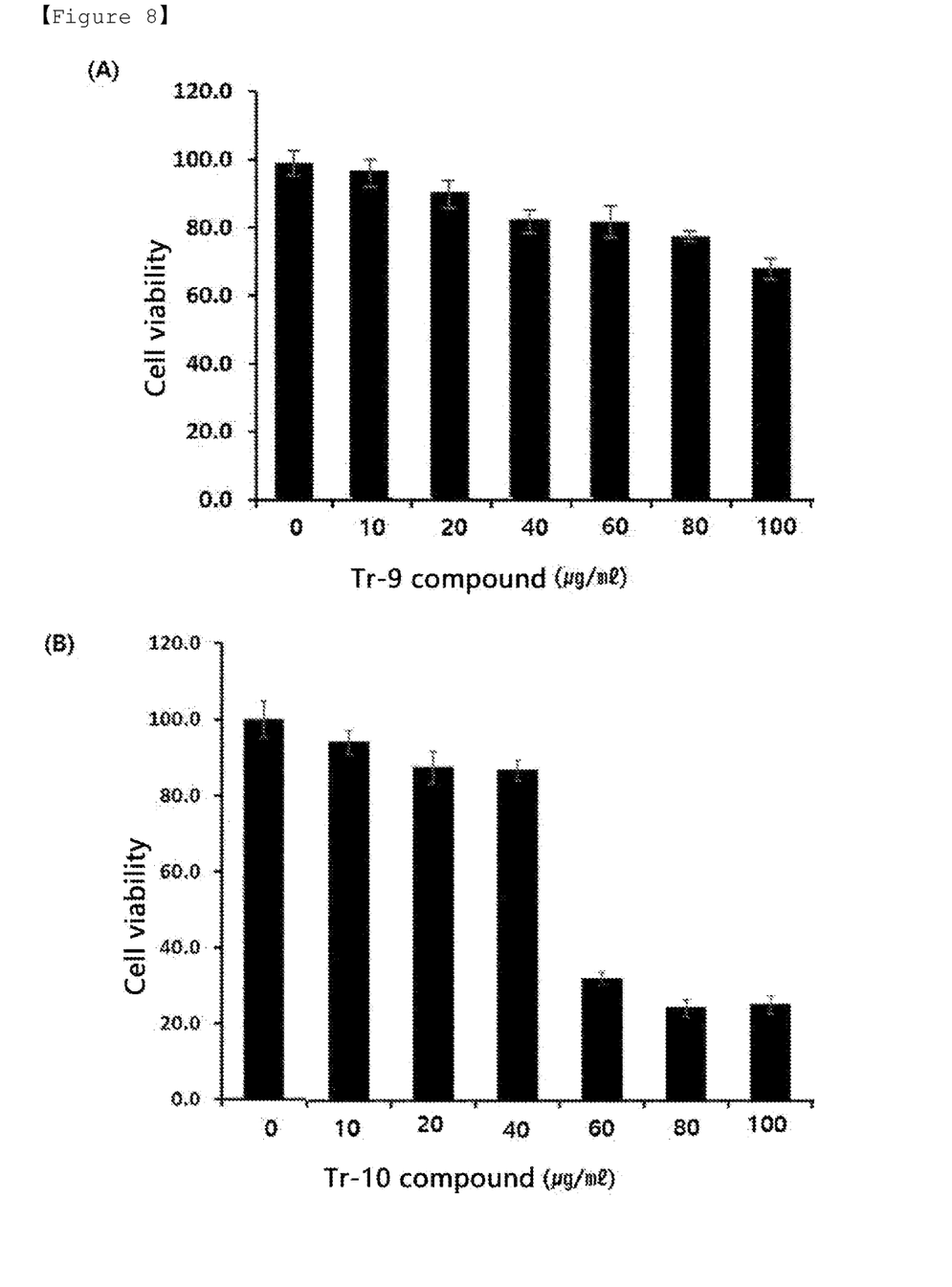
FIG. 8 shows cell viability of the pancreatic cancer cell line(BxPC3) according to the treatment by concentration of the Tr-9 compound(A) and the Tr-10 compound(B).

Then, the compound purely isolated from the n-hexane fraction of the Torilidis Fructus extract was subjected to mass spectrometry and 400 MHz FT-NMR spectrometer (Varian, USA) to confirm the structure of the novel compound of Formula 1 (Tr-9) and diacetyl torilin of Formula 2 (Tr-10) (FIGS. 1 and 2).

[Formula 1]

EXAMPLE 2. CONFIRMATION OF ANTICANCER EFFECT OF COMPOUNDS TR-9 AND TR-10 (WST-1 ASSAY)

The cytotoxicity of the Tr-9 compound to six cancer cell lines was confirmed. Lung cancer(A549), gastric cancer (AGS), liver cancer(Hep3B)), breast cancer(MDA-MB-231), colorectal cancer(HCT116) and pancreatic cancer (BxPC-3) cell lines and fibroblasts were aliquoted in a 96-well plate in an amount of $5 \times 10^3$ cells/well, and the novel compound Tr-9 was treated thereto at a concentration of 10, 20, 40, 60, 80, 100 µg/mℓ for 24 hours, respectively. Lung cancer cell line was further treated at a concentration of 100 µg/mℓ for 24 hours, 48 hours and 72 hours.

Then, the amount of living cells was measured using WST(high sensitive Water Soluble Tetrazolium salt). WST reacts with dehydrogenase in living cells and produces orange-colored water-soluble formazan. Since dehydrogenase that reacts with WST is an enzyme present in the mitochondrial electron transport chain of metabolically active cells and is effective only in living cells, the production of formazan is proportional to the number of living cells. Therefore, the absorbance at 450 nm was measured to confirm the cell viability through the formation of formazan.

Figure 9:
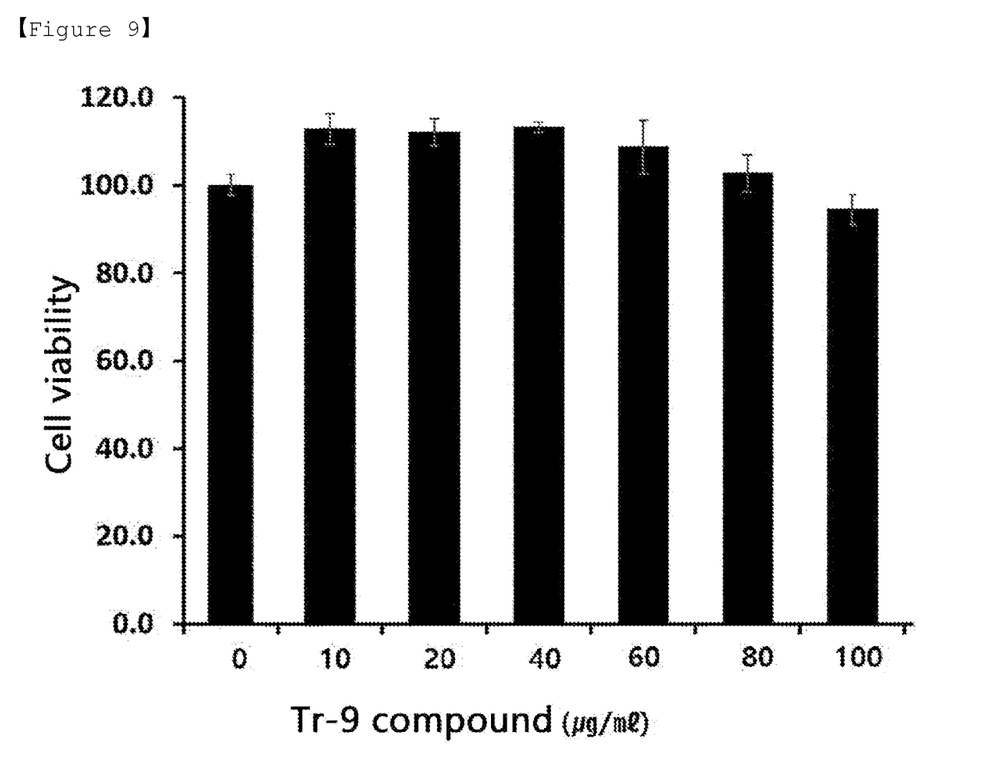
FIG. 9 shows cell viability of Human fibroblast according to the treatment by concentration of the Tr-9 compound..

As a result, as shown in FIGS. 3 to 8, it was confirmed that the compound Tr-9 of the present invention (compound of Formula 1) or the compound Tr-10 (compound of Formula 2) decreases the cell viability for lung cancer, stomach cancer, gastric cancer, liver cancer, breast cancer, colorectal cancer and pancreatic cancer cells. As shown in FIG. 9, it was confirmed that the Tr-9 compound shows little change in the cell viability of human fibroblast. Therefore, it was confirmed that there is an anticancer activity that specifically kills cancer cells such as lung cancer, gastric cancer, liver cancer, breast cancer, colorectal cancer and pancreatic cancer without affecting normal cells.

EXAMPLE 3. CONFIRMATION OF ANTICANCER EFFECT ON LUNG CANCER ACCORDING TO ORAL ADMINISTRATION OF COMPOUND TR-9 USING ANIMAL MODEL

Anticancer activity against lung cancer according to the oral administration of Tr-9 was confirmed through a nude mouse xenograft model of human lung cancer cells (A549). Specific pathogen-free (SPF) nude mice of the BALB/C strain were used as the animal model. Animals were bred in the animal room of Daedeok Campus of Hannam University maintained at a temperature of 23±3° C., relative humidity of 55±15%, ventilation frequency of 10-20 times/hr, lighting time of 12 hours(lights on at 8 am and off at 8 pm) and illuminance of 150 to 300 Lux.

For cancer cell transplantation, all cells were collected and counted on the last day of culture, and the concentration of human lung cancer cell line A549 was adjusted to $5 \times 10^6$ cells/ml using PBS. The adjusted cell culture solution was injected subcutaneously into the auxiliary region between the right scapula and chest wall at 0.2 ml ($1 \times 10^6$ cells/mouse) per mouse.

The Tr-9 was dissolved in sterile PBS and 1 mM Tr-9 200 µℓ was orally administered per mouse once a day, and all animals were weighed immediately before the start of drug (Tr-9) administration and 10 times in total from day 2 to day 23 after cancer cell transplantation (Table 1).

As a result, as shown in Table 1 below, it was found that there was almost no difference in body weight according to the administration of the drugs(Tr-9 and torilin).

TABLE 1

Change in mouse weight

| Group (n = 4) | 0 Day | 2 Days | 5 Days | 7 Days | 9 Days | 12 Days | 14 Days | 16 Days | 19 Days | 21 Days | 23 Days |
|---|---|---|---|---|---|---|---|---|---|---|---|
| Control | 100.0 ± 0.0 | 101.3 ± 1.0 | 99.1 ± 1.9 | 101.3 ± 1.3 | 103.4 ± 1.5 | 100.8 ± 1.7 | 100.4 ± 3.6 | 102.6 ± 4.4 | 100.2 ± 3.7 | 102.2 ± 3.7 | 104.2 ± 4.0 |
| Torilin | 100.0 ± 0.0 | 100.0 ± 3.0 | 97.2 ± 2.5 | 99.5 ± 3.5 | 105.7 ± 7.0 | 101.0 ± 6.2 | 101.8 ± 5.5 | 103.9 ± 5.8 | 101.1 ± 5.8 | 102.9 ± 6.0 | 105.0 ± 7.1 |
| Tr-9 | 100.0 ± 0.0 | 95.6 ± 1.7 | 96.9 ± 1.8 | 99.5 ± 1.5 | 102.3 ± 2.8 | 98.6 ± 1.5 | 100.7 ± 3.6 | 102.5 ± 3.8 | 103.6 ± 5.5 | 102.9 ± 5.7 | 104.7 ± 5.6 |

In Table 1 above, data values are the mean ± standard deviation. After measuring the body weight, the animals were killed using $CO_2$ gas, and the tumor was separated and the size was measured in 3 directions using a vernier caliper for each animal. Then, the change in tumor size was expressed as a calculated value of (length×width×height)/2 (Table 2).

Figure 10:
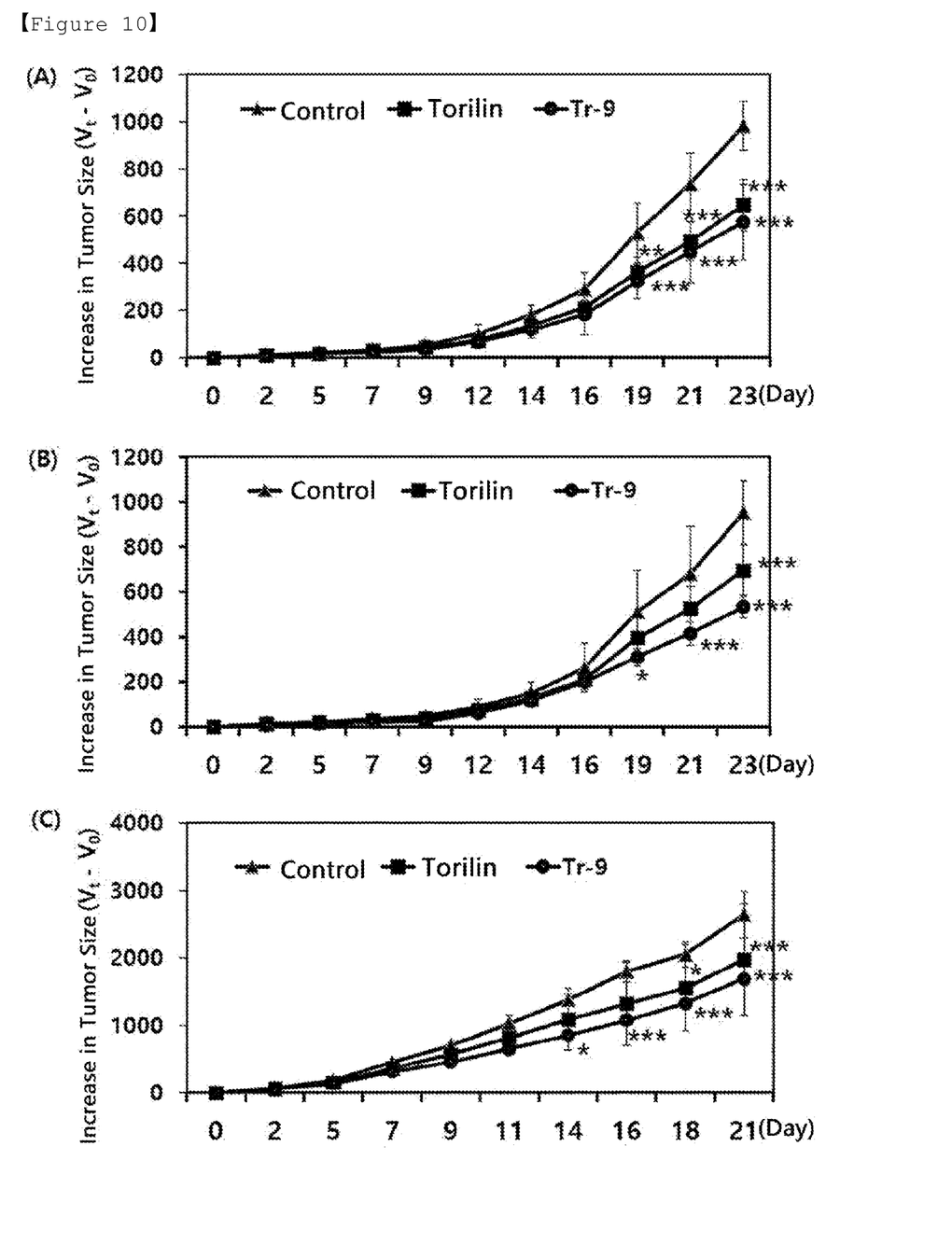
FIG. 10 is a result of confirming the change in tumor size according to oral and intraperitoneal administration of the Tr-9 compound using lung cancer and colorectal cancer animal models. (A) is a change in tumor size after oral administration of the Tr-9 compound to a lung cancer animal model, (B) is a change in tumor size after intraperitoneal administration of the Tr-9 compound to a lung cancer animal model, (C) is a change in tumor size after intraperitoneal administration of the Tr-9 compound to a colorectal cancer animal model. *, , * indicates that the tumor size increase in the group administered with torilin or the Tr-9 compound of the present invention was statistically significantly reduced compared to the control group, and * is $p<0.05$,  is $p<0.01$, and * is $p<0.001$.

As shown in Table 2 below and FIG. 10, the tumor size gradually increased after tumor cell transplantation. When compared by date, it was found that the tumor size in the group administered with the torilin and the Tr-9 was found to be smaller than that of the control group, and after day 19, the tumor size in the group administered with the torilin and the Tr-9 of the present invention compared to the control group The size was statistically significantly smaller than that of the control group. That is, the growth of cancer cells was inhibited by the oral administration of the torilin and the Tr-9 of the present invention. Furthermore, it was confirmed that the tumor size in the group orally administered with the Tr-9 of the present invention was further reduced by 6% to 7% compared to the group orally administered with the torilin.

On the other hand, as shown in Table 3, it was confirmed that the tumor weight on day 23 in the group orally administered with the Tr-9 compound of the present invention was reduced by about 36% compared to the control group not treated with anything.

TABLE 2

Change in tumor size

Tumor size increase ($V_t - V_0$)

| Group (n = 4) | Control | Torilin | Inhibition rate of torilin (%) | Tr-9 | Inhibition rate of Tr-9 (%) |
|---|---|---|---|---|---|
| Day 0 | 0.0 ± 0.0 | 0.0 ± 0.0 | — | 0.0 ± 0.0 | — |
| Day 2 | 12.1 ± 14.5 | 11.4 ± 11.7 | 5.8 | 5.4 ± 1.4 | 55.4 |

TABLE 2-continued

Change in tumor size

Tumor size increase ($V_t - V_0$)

| Group (n = 4) | Control | Torilin | Inhibition rate of torilin (%) | Tr-9 | Inhibition rate of Tr-9 (%) |
|---|---|---|---|---|---|
| Day 5  | 20.3 ± 12.1   | 18.1 ± 9.4      | 10.8 | 13.9 ± 6.1       | 31.5 |
| Day 7  | 32.4 ± 13.0   | 28.6 ± 3.0      | 11.7 | 24.0 ± 14.5      | 25.9 |
| Day 9  | 53.1 ± 20.8   | 42.0 ± 9.8      | 20.9 | 36.5 ± 12.5      | 31.3 |
| Day 12 | 101.9 ± 39.8  | 74.4 ± 31.5     | 27.0 | 67.8 ± 25.4      | 33.5 |
| Day 14 | 182.0 ± 41.8  | 134.6 ± 37.6    | 26.0 | 119.9 ± 37.5     | 34.1 |
| Day 16 | 290.2 ± 72.3  | 211.8 ± 32.9    | 27.0 | 183.4 ± 85.6     | 36.8 |
| Day 19 | 528.8 ± 127.3 | 362.2 ± 64.2 ** | 31.5 | 322.8 ± 71.3 *** | 39.0 |
| Day 21 | 736.4 ± 130.7 | 493.4 ± 82.6 ***| 33.0 | 448.2 ± 131.2 ***| 39.2 |
| Day 23 | 981.9 ± 104.3 | 646.9 ± 108.8 ***| 34.1| 575.0 ± 159.7 ***| 41.4 |

TABLE 3

Tumor weight at Day 23 following administration of torilin and Tr-9 compound of the present invention

| Group (n = 4) | Tumor weight at Day 23 (mg) | Tumor weight reduction rate compared to control group (%) |
|---|---|---|
| Control | 1.057 ± 0.145 | — |
| Torilin | 0.745 ± 0.196 | 29.5 |
| Tr-9 | 0.676 ± 0.185* | 36.0 |

In Table 2 and Table 3 above, data values are the mean ± standard deviation. *, , and * indicate that the increase in the tumor size or the tumor weight of the torilin or Tr-9 administration group was statistically significantly reduced compared to the control group, and * is p<0.05,  is p<0.01, and * is p<0.001. Tumor size increase is ($\Delta t$)=$V_t$-$V_o$, wherein $V_t$ is the value of measuring the tumor size by date, and $V_o$ is the value of measuring the initial tumor size.

of 55±15%, ventilation frequency of 10-20 times/hr, lighting time of 12 hours(lights on at 8 am and off at 8 pm) and illuminance of 150 to 300 Lux.

For cancer cell transplantation, all cells were collected and counted on the last day of culture, and the concentration of human lung cancer cell line A549 was adjusted to $5 \times 10^6$ cells/ml using PBS. The adjusted cell culture solution was injected subcutaneously into the auxiliary region between the right scapula and chest wall at 0.2 ml ($1 \times 10^6$ cells/mouse) per mouse.

The Tr-9 was dissolved in sterile PBS and 1 mM Tr-9 200 μe was intraperitoneally administered per mouse once a day, and all animals were weighed immediately before the start of drug (Tr-9) administration and 10 times in total from day 2 to day 23 after cancer cell transplantation (Table 4).

As a result, as shown in Table 4 below, it was found that there was almost no difference in body weight according to the administration of the drugs(Tr-9 and torilin).

TABLE 4

Change in mouse weight

Days after drug treatment

| Group (n = 4) | 0 Day | 2 Days | 5 Days | 7 Days | 9 Days | 12 Days | 14 Days | 16 Days | 19 Days | 21 Days | 23 Days |
|---|---|---|---|---|---|---|---|---|---|---|---|
| Control | 100.0 ± 0.0 | 100.3 ± 2.1 | 99.1 ± 2.8 | 105.1 ± 3.4 | 104.2 ± 0.8 | 102.2 ± 3.7 | 100.2 ± 2.1 | 104.0 ± 2.4 | 103.3 ± 2.6 | 104.7 ± 3.7 | 107.8 ± 5.2 |
| Torilin | 100.0 ± 0.0 | 98.2 ± 1.5 | 98.2 ± 1.4 | 97.6 ± 1.0 | 102.7 ± 2.7 | 101.0 ± 3.1 | 101.2 ± 2.6 | 102.3 ± 3.8 | 103.4 ± 5.2 | 102.9 ± 4.1 | 105.0 ± 4.6 |
| Tr-9 | 100.0 ± 0.0 | 98.2 ± 1.0 | 94.7 ± 2.5 | 94.1 ± 2.2 | 99.7 ± 2.7 | 96.7 ± 3.1 | 97.3 ± 2.8 | 100.2 ± 1.8 | 98.3 ± 2.9 | 99.4 ± 1.6 | 100.2 ± 2.6 |

EXAMPLE 4. CONFIRMATION OF ANTICANCER EFFECT ON LUNG CANCER ACCORDING TO INTRAPERITONEAL ADMINISTRATION OF COMPOUND TR-9 USING ANIMAL MODEL

Anticancer activity against lung cancer according to the intraperitoneal administration of Tr-9 was confirmed through a nude mouse xenograft model of human lung cancer cells (A549). In Example 4, it was carried out using the same animal model and method as the oral administration, except that it was administered intraperitoneally.

Specific pathogen-free (SPF) nude mice of the BALB/C strain were used as the animal model. Animals were bred in the animal room of Daedeok Campus of Hannam University maintained at a temperature of 23±3° C., relative humidity In Table 4 above, data values are the mean ± standard deviation. After measuring the body weight, the animals were killed using $CO_2$ gas, and the tumor was separated and the size was measured in 3 directions using a vernier caliper for each animal. Then, the change in tumor size was expressed as a calculated value of (length×width×height)/2 (Table 4).

As shown in Table 5 below and FIG. 10, the tumor size gradually increased after tumor cell transplantation. When compared by date, it was found that the tumor size in the group administered with the torilin and the Tr-9 was found to be smaller than that of the control group, and after day 19, the tumor size in the group administered with the torilin and the Tr-9 of the present invention compared to the control group The size was statistically significantly smaller than that of the control group. That is, the growth of cancer cells was inhibited by the intraperitoneal administration of the Tr-9 of the present invention. It was confirmed that the tumor size in the group intraperitoneally administered with the Tr-9 of the present invention was further reduced by about 17% compared to the group intraperitoneally administered with the torilin.

On the other hand, as shown in Table 6, it was confirmed that the tumor weight on day 23 in the group intraperitoneally administered with the Tr-9 compound of the present invention was reduced by about 53% compared to the control group not treated with anything.

TABLE 5

Change in tumor size

Tumor size increase ($V_t - V_0$)

| Group (n = 4) | Control | Torilin | Inhibition rate of torilin (%) | Tr-9 | Inhibition rate of Tr-9 (%) |
|---|---|---|---|---|---|
| Day 0 | 0.0 ± 0.0 | 0.0 ± 0.0 | — | 0.0 ± 0.0 | — |
| Day 2 | 13.6 ± 11.2 | 13.2 ± 13.2 | 2.9 | 7.0 ± 5.4 | 48.5 |
| Day 5 | 20.9 ± 13.0 | 19.9 ± 10.4 | 4.8 | 13.8 ± 8.5 | 34.0 |
| Day 7 | 33.9 ± 9.1 | 28.9 ± 12.5 | 14.7 | 19.6 ± 10.1 | 42.2 |
| Day 9 | 45.8 ± 11.6 | 38.0 ± 8.1 | 17.0 | 24.4 ± 7.1 | 46.7 |
| Day 12 | 87.9 ± 36.6 | 75.1 ± 10.7 | 14.6 | 61.1 ± 7.0 | 30.5 |
| Day 14 | 150.5 ± 50.9 | 127.0 ± 25.8 | 15.6 | 116.4 ± 15.1 | 22.7 |
| Day 16 | 262.9 ± 108.6 | 210.5 ± 44.8 | 19.9 | 198.3 ± 22.8 | 24.6 |
| Day 19 | 511.9 ± 183.9 | 394.8 ± 93.5 | 22.9 | 309.2 ± 39.5 * | 39.6 |
| Day 21 | 679.2 ± 213.1 | 525.2 ± 99.1 | 22.7 | 415.2 ± 53.1 *** | 38.9 |
| Day 23 | 952.7 ± 140.4 | 695.0 ± 110.6 *** | 27.0 | 531.8 ± 46.5 *** | 44.2 |

TABLE 6

Tumor weight at Day 23 following administration of torilin and Tr-9 compound of the present invention

| Group (n = 4) | Tumor weight at Day 23 (mg) | Tumor weight reduction rate compared to control group (%) |
|---|---|---|
| Control | 1.358 ± 0.145 | — |
| Torilin | 0.970 ± 0.183 | 28.6 |
| Tr-9 | 0.641 ± 0.100 * | 52.8 |

In Table 5 and Table 6 above, data values are the mean ± standard deviation. * and *** indicate that the increase in the tumor size or the tumor weight of the torilin or Tr-9 administration group was statistically significantly reduced compared to the control group, and * is p<0.05 and *** is p<0.001. Tumor size increase is ($\Delta t$)=$V_t$-$V_o$, wherein $V_t$ is the value of measuring the tumor size by date, and $V_o$ is the value of measuring the initial tumor size.

EXAMPLE 5. CONFIRMATION OF ANTICANCER EFFECT ON COLORECTAL CANCER ACCORDING TO INTRAPERITONEAL ADMINISTRATION OF COMPOUND TR-9 USING ANIMAL MODEL

Anticancer activity against colorectal cancer according to the intraperitoneal administration of Tr-9 was confirmed through a nude mouse xenograft model of human colorectal cancer cells (HCT116). In Example 5, Example 4 was repeated except for using colorectal cancer cells.

Specific pathogen-free (SPF) nude mice of the BALB/C strain were used as the animal model. Animals were bred in the animal room of Daedeok Campus of Hannam University maintained at a temperature of 23±3° C., relative humidity of 55±15%, ventilation frequency of 10-20 times/hr, lighting time of 12 hours(lights on at 8 am and off at 8 pm) and illuminance of 150 to 300 Lux.

For cancer cell transplantation, all cells were collected and counted on the last day of culture, and the concentration of human colorectal cancer cell line HCT116 was adjusted to $5 \times 10^6$ cells/ml using PBS. The adjusted cell culture solution was injected subcutaneously into the auxiliary region between the right scapula and chest wall at 0.2 ml ($1 \times 10^6$ cells/mouse) per mouse.

The Tr-9 was dissolved in sterile PBS and 1 mM Tr-9 200 μe was intraperitoneally administered per mouse once a day, and all animals were weighed immediately before the start of drug (Tr-9) administration and 9 times in total from day 2 to day 21 after cancer cell transplantation (Table 7).

As a result, as shown in Table 7 below, it was found that there was almost no difference in body weight according to the administration of the drugs(Tr-9 and torilin).

TABLE 7

Change in mouse weight

Days after drug treatment

| Group (n = 4) | 0 Day | 2 Days | 5 Days | 7 Days | 9 Days | 11 Days | 14 Days | 16 Days | 18 Days | 21 Days |
|---|---|---|---|---|---|---|---|---|---|---|
| Control | 100.0 ± 0.0 | 98.1 ± 2.5 | 98.7 ± 1.6 | 96.3 ± 2.7 | 95.9 ± 5.0 | 95.6 ± 4.8 | 96.8 ± 6.3 | 98.4 ± 6.4 | 100.3 ± 6.8 | 103.0 ± 8.4 |
| Torilin | 100.0 ± 0.0 | 100.5 ± 1.8 | 101.4 ± 2.7 | 98.4 ± 2.7 | 98.4 ± 2.8 | 98.8 ± 3.2 | 98.2 ± 4.3 | 98.6 ± 4.9 | 100.0 ± 5.3 | 101.8 ± 7.3 |
| Tr-9 | 100.0 ± 0.0 | 99.7 ± 1.7 | 100.5 ± 3.2 | 99.9 ± 4.1 | 99.8 ± 4.9 | 98.6 ± 3.5 | 99.7 ± 4.5 | 98.5 ± 6.0 | 100.4 ± 5.5 | 102.4 ± 7.0 |

In Table 7 above, data values are the mean ± standard deviation. After measuring the body weight, the animals were killed using $CO_2$ gas, and the tumor was separated and the size was measured in 3 directions using a vernier caliper for each animal. Then, the change in tumor size was expressed as a calculated value of (length×width×height)/2 (Table 8).

As shown in Table 8 below and FIG. 10, the tumor size gradually increased after tumor cell transplantation. When compared by date, it was found that the tumor size in the group administered with the torilin and the Tr-9 was found to be smaller than that of the control group, and after day 14, the tumor size in the group administered with the torilin and the Tr-9 of the present invention compared to the control group The size was statistically significantly smaller than that of the control group. That is, the growth of colorectal cancer cells was inhibited by the intraperitoneal administration of the Tr-9 of the present invention. It was confirmed that the tumor size in the group intraperitoneally administered with the Tr-9 of the present invention was further reduced by about 10% compared to the group intraperitoneally administered with the torilin.

On the other hand, as shown in Table 9, it was confirmed that the tumor weight on day 21 in the group intraperitoneally administered with the Tr-9 compound of the present invention was reduced by about 36% compared to the control group not treated with anything.

TABLE 8

Change in tumor size

Tumor weight increase ($V_t - V_o$)

| Group (n = 4) | Control | Torilin | Inhibition rate of torilin (%) | Tr-9 | Inhibition rate of Tr-9 (%) |
|---|---|---|---|---|---|
| Day 0  | 0.0 ± 0.0 | 0.0 ± 0.0 | — | 0.0 ± 0.0 | — |
| Day 2  | 66.2 ± 12.9 | 54.7 ± 16.2 | 17.4 | 53.1 ± 17.9 | 19.8 |
| Day 5  | 180.8 ± 37.5 | 151.4 ± 33.3 | 16.3 | 139.4 ± 40.3 | 22.9 |
| Day 7  | 447.0 ± 49.4 | 362.7 ± 59.4 | 18.9 | 312.6 ± 71.9 | 30.1 |
| Day 9  | 699.1 ± 70.7 | 565.9 ± 142.4 | 19.1 | 453.9 ± 112.5 | 35.1 |
| Day 11 | 1029.3 ± 115.5 | 816.9 ± 248.1 | 20.6 | 648.7 ± 112.0 | 37.0 |
| Day 14 | 1378.0 ± 81.8 | 1086.2 ± 458.4 | 21.2 | 849.8 ± 110.2 | 38.3 |
| Day 16 | 1796.7 ± 156.9 | 1319.9 ± 614.0 | 26.5 | 1075.9 ± 155.6*** | 40.1 |
| Day 18 | 2047.9 ± 183.8 | 1555.6 ± 640.5* | 24.0 | 1326.9 ± 216.2*** | 35.2 |
| Day 21 | 2638.0 ± 345.6 | 1973.3 ± 821.1*** | 25.2 | 1690.3 ± 144.2*** | 35.9 |

TABLE 9

Tumor (colorectal cancer) weight at Day 21 following intraperitoneal administration of torilin and Tr-9 compound of the present invention

| Group (n = 4) | Tumor weight at Day 21 (mg) | Tumor weight reduction rate compared to control group (%) |
|---|---|---|
| Control | 3.841 ± 0.919 | — |
| Torilin | 2.846 ± 0.834 | 25.9 |
| Tr-9 | 2.476 ± 0.308* | 35.5 |

In Table 8 and Table 9 above, data values are the mean ± standard deviation. * and *** indicate that the increase in the tumor size of the torilin or Tr-9 administration group was statistically significantly reduced compared to the control group, and * is $p<0.05$ and *** is $p<0.001$. Tumor size increase is $(\Delta t) = V_t - V_o$, wherein $V_t$ is the value of measuring the tumor size by date, and $V_o$ is the value of measuring the initial tumor size.

The invention claimed is:

1. A compound represented by the following Formula 1 or a pharmaceutically acceptable salt thereof

[Formula 1]

2. An anticancer pharmaceutical composition comprising a torilin derivative compound represented by the following Formula 1 or Formula 2, or a pharmaceutically acceptable salt thereof, as an active ingredient

[Formula 1]

[Formula 2]

[Formula 1]

[Formula 2]

3. The anticancer pharmaceutical composition according to claim 2, wherein the anticancer is to at least one cancer selected from lung cancer, gastric cancer, liver cancer, breast cancer, colorectal cancer and pancreatic cancer.

4. The anticancer pharmaceutical composition according to claim 2, wherein the torilin derivative compound represented by the Formula 1 or Formula 2 is isolated from Torilidis Fructus.

5. The anticancer pharmaceutical composition according to claim 2, which further comprises a carrier, an excipient or a diluent in addition to the active ingredient.

6. An anticancer health functional food composition comprising a torilin derivative compound represented by the following Formula 1 or Formula 2, or a food acceptable salt thereof, as an active ingredient 7. The anticancer health functional food composition according to claim 6, which further comprises at least one selected from nutrients, vitamins, electrolytes, a flavoring agent, a colorant, a thickening agent, pectic acid and a salt thereof, alginic acid and a salt thereof, organic acids, a protective colloidal thickening agent, a pH adjusting agent, a stabilizer, a preservative, glycerin, alcohols, and carbonating agents used in carbonated beverages in addition to the active ingredient.

* * * * *